United States Patent [19]
Starley

[11] Patent Number: 5,158,556
[45] Date of Patent: Oct. 27, 1992

[54] CONDOM RETAINING APPARATUS

[76] Inventor: Merlyn Starley, 50 Chumasero Dr., #10F, San Francisco, Calif. 94132

[21] Appl. No.: 745,832

[22] Filed: Aug. 16, 1991

[51] Int. Cl.⁵ .......................... A61F 5/44; A61F 6/02; A61F 6/04
[52] U.S. Cl. .................... 604/351; 128/842; 128/844; 604/346; 604/347; 604/349
[58] Field of Search ............... 128/157, 158, 842, 844, 128/883, 110.1, 124.1, 169, 171; 604/349, 351, 353, 346–347; 602/12, 16, 36, 41, 58, 78; 206/69

[56] References Cited

U.S. PATENT DOCUMENTS

| | | |
|---|---|---|
| 731,201 | 6/1903 | Miller et al. |
| 1,982,520 | 11/1934 | Jakala |
| 2,222,825 | 11/1940 | Starck |
| 2,379,346 | 6/1945 | Farrell |
| 3,999,550 | 12/1976 | Martin |
| 4,354,494 | 10/1982 | Hogin ................... 128/844 |
| 4,810,247 | 3/1989 | Glassman ............. 604/171 |
| 4,834,114 | 5/1989 | Boarman .............. 604/347 |
| 4,840,624 | 6/1989 | Lee ....................... 604/349 |
| 4,966,594 | 10/1990 | Thomas ................ 604/353 |
| 5,076,287 | 12/1991 | Johnson ............... 128/844 |

FOREIGN PATENT DOCUMENTS 454773 1/1928 Fed. Rep. of Germany .
992462 10/1951 France .
1508356 11/1967 France .

Primary Examiner—David Isabella
Assistant Examiner—A. Zuttarelli
Attorney, Agent, or Firm—Thomas I. Rozsa

[57] ABSTRACT

The present invention is a condom retaining apparatus. It comprises a pair of double-sided flexible thin bands each having a first end and a second end, and small U-shaped clipping members for attaching the first ends of the pair of double-sided flexible thin bands to the condom ring of a condom at two opposite locations. Each double-sided flexible thin band has adhesive at one side for attaching it to a user's skin on the upper thigh areas. The condom retaining apparatus is designed to keep the condom in its unrolled position while it is being used, without tearing the condom and without being uncomfortable to the user.

6 Claims, 2 Drawing Sheets (Section on line 3 - 3)

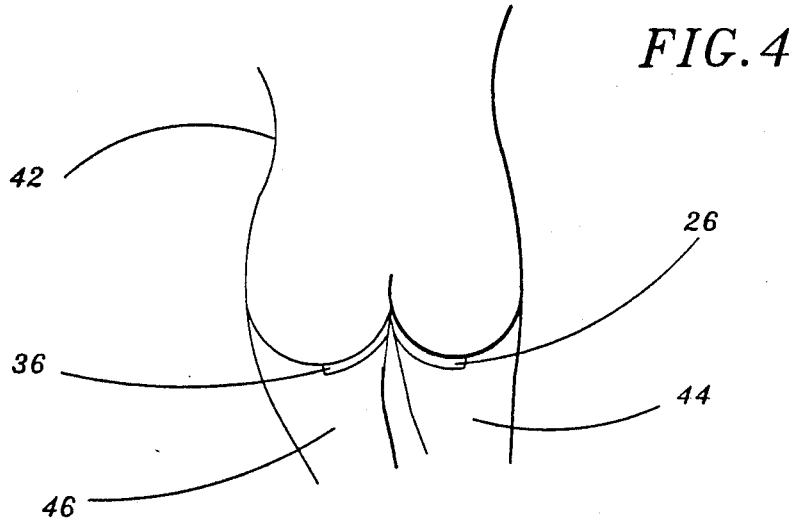
FIG. 4
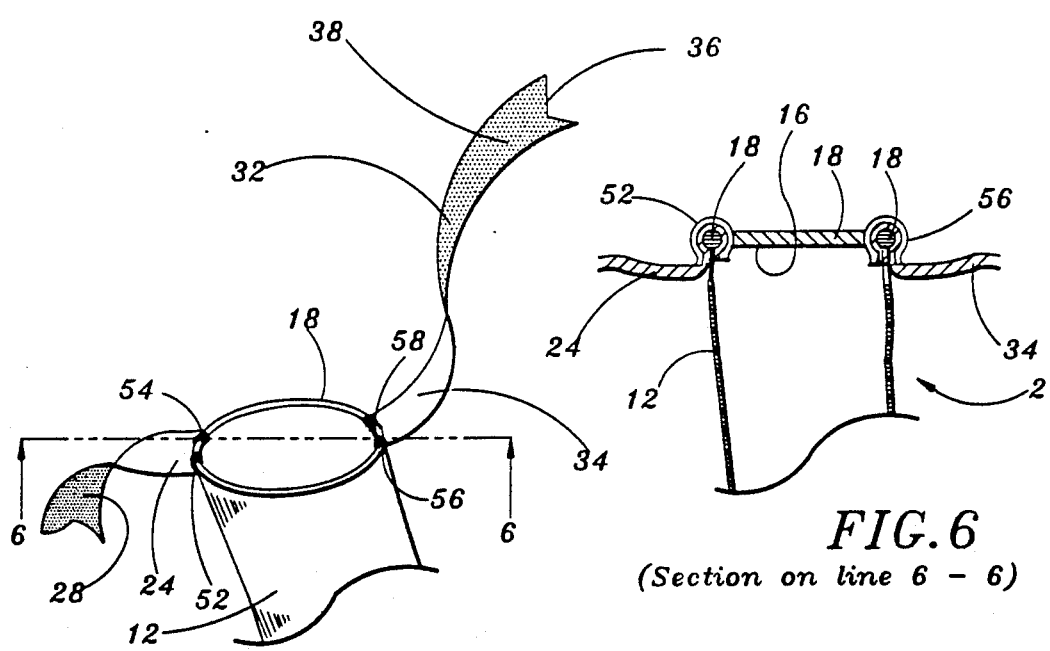
FIG. 5
FIG. 6
(Section on line 6 - 6)

CONDOM RETAINING APPARATUS

BACKGROUND OF THE INVENTION

1. Field of the Invention

The present invention relates to the field of apparatus for retaining a health care or medical treatment appliance to the lower body of a man. More particularly, the present invention relates to the field of condom retaining apparatus.

2. Description of the prior Art

Many people use condoms during sexual intercourse. One problem of using condoms encountered by some people is that sometimes a condom does not remain in its fully unrolled condition on the penis of a man while it is in use, and subsequently becomes loose. This situation often jeopardizes the purpose of using the condom. Therefore, it is desirable to have a retaining apparatus to keep the condom in its fully unrolled condition while in use.

The following prior art patents have been found to be relevant to the field of the present invention:

1. U.S. Pat. No. 3,999,550 issued to Martin on Dec. 28, 1976 for "External Male Catheter" (hereafter the "Martin Patent").

2. U.S. Pat. No. 2,379,346 issued to Farrell on Jun. 26, 1945 for "Urinary Appliance" (hereafter the "Farrell Patent").

3. U.S. Pat. No. 2,222,825 issued to Starck on Nov. 26, 1940 for "Urinal Pouch" (hereafter the "Starck Patent").

4. U.S. Pat. No. 1,982,520 issued to Jakala on Nov. 27, 1934 for "Sanitary Device" (hereafter the "Jakala Patent").

5. U.S. Pat. No. 731,201 issued to Miller et al. on Jun. 16, 1903 for "Supporting Bandage" (hereafter the "Miller Patent").

6. French Patent No. 1,508,356 issued to Rasumny on Nov. 27, 1967 for "Apparatus For Unitary Incontinence In Men" (hereafter the "Rasumny Patent").

7. French Patent No. 992,462 issued to Gamard et al. on Oct. 18, 1951 for "Apparatus For The Treatment of Unitary Incontinence" (hereafter the "Gamard Patent").

8. German Patent No. 454,773 issued to Köhler on Jan. 17, 1928 for "Apparatus For Treatment of Male Infectious Diseases" (hereafter the "Köhler Patent").

The Miller Patent (1903) discloses a supporting bandage for retaining a medicated or absorbent compress 1 on the head of the penis of a man. The supporting bandage comprises a waist belt 6 to be wrapped around the man's waist, and a pair of flexible elastic strings 5 linking the compress 1 to the waist belt 6. The Miller Patent supporting bandage is not suitable for the purpose of retaining a condom in its fully unrolled condition, because it merely holds the compress 1 on the head of the penis in a relatively motionless situation. If the same supporting bandage is used for a condom, then the flexibility and elasticity of the pair of strings 5 will allow the condom to get loose as a result of the body movements during sexual intercourse.

The Köhler Patent (1928) discloses an apparatus for treatment of male infectious diseases. The apparatus comprises a generally oval-shaped rigid container 1 attached to belt support 11 by an attachment assembly. The attachment assembly includes a cap member 10, a disc member 4 and a ring member 6 which is threaded on the neck 2 of the container 1. The Köhler Patent attachment assembly is designed for mounting a rigid container, which makes it unfit for retaining a flexible condom.

The Jakala Patent (1934) discloses a sanitary device which again comprises an oval-shaped rigid container 11 made of metal material. The rigid container 11 is attached to the penis of a man by a wiring member 13. The spring tension of the wiring member holds it inside the cavity of the rigid container 11. It is clear that this arrangement is also not suitable for a condom.

The Starck patent (1940) discloses a large sized urinal pouch 5 for covering the entire lower body area of a patient with bladder disability. The urinal pouch 5 is retained under the lower body portion between the two legs of the patient by a number of strap and buckle assemblies.

The Farrell Patent (1945) discloses a urinary appliance for people having urinary problems. It comprises a rubber tube 15 attached to the penis of a man by an attachment assembly. The attachment assembly includes a rigid or semirigid tubular member 10 having a circular flange 11. There are two pairs of studs 12 and 13 on the circular flange 11 for connection with a pair of short straps 7 and a pair of long straps 8, which straps 7 and 8 are all further attached to a waist belt 6.

The Gamard Patent (1951) discloses an apparatus for treatment of urinary incontinence. The apparatus comprises a container 1 having an enlarged flange 2 attached to a waist belt 4 through straps 3. The apparatus also includes an electronic treatment device 16 which has two terminals connected into the container 1.

The Rasumny Patent (1967) discloses an apparatus for urinary incontinence in men, where a tubular container 1 is retained to the penis by a band 6 which is wrapped around the end of the tubular container and fastened by VELCRO-R members. A pair of short straps 9 and 9' then connect the fastened band 6 to a waist belt 7.

The Martin Patent (1976) discloses an external male catheter 22 which is retained on the user's penis by a belt assembly 28. A belt receptacle 24 and a belt retaining ring 26 are used for connecting the catheter 22 and the belt assembly 28.

It can be seen that none of the prior art apparatus is suitable for the purpose of retaining a condom on a man's penis while it is in use. Some of the prior art patents are designed with a rigid container, such as the Köhler Patent and the Jakala Patent, which is certainly not suitable for the highly elastic and flexible condom. Some of the prior art patents are designed with rigid or protruding attachment members, such as the buckles of the Starck Patent, the flange and studs of the Farrell patent, and the belt receptacle and belt retaining ring of the Martin Patent, which are also not suitable for retaining a condom because the rigid or extended members will make the user of the condom uncomfortable. Other prior art patents, such as the Miller Patent, the Gamard Patent and the Rasumny Patent, use short flexible straps to connect the containers to the waist belts. As discussed before, the disadvantage of this type of arrangement is that even though the waist belt is tightly fastened to a user's waist, the short connecting straps themselves are dangling but not fastened to the user's body. They will not withstand the movements during sexual intercourse, since their flexibility and elasticity will make them act just like a swing to permit a condom to get loose.

Therefore there is an existing need to have a condom retaining apparatus which securely keeps the condom in its unrolled position while being used, yet is not uncomfortable for the user. This need is particularly urgent in today's society, where a rapidly growing number of people are using the condoms for various purposes, including preventing the transmittal of sexually communicable diseases, such as AIDS.

SUMMARY OF THE INVENTION

The present invention is a condom retaining apparatus.

It has been discovered, according to the present invention, that for the purpose of holding the condom in its unfolded position during sexual intercourse, it is essential to retain the open end of the condom as close to the body end of the penis of the user as possible. Since condoms are made of very thin rubber type material, it is important to attach the retaining apparatus to the condom without tearing it. Usually a condom has a condom ring around its open end. It is therefore an object of the present invention to condom ring of a condom, so the chance of tearing the condom is greatly reduced.

It has further been discovered, according to the present invention, that to prevent the open end of the condom from rolling back toward its tip, the retaining members of the condom retaining apparatus should be affixed to the body of the user at locations immediately adjacent to the body end of the penis of the user. Any flexible loose portion of a connecting strap from the point of attachment to a waist belt, as in some of the prior art patents, will allow the connecting strap to swing, which in turn will allow the condom to get loose. Therefore, it is a further object of the present invention to eliminate any loose connecting strap and directly fasten the end of the condom to the immediately adjacent body part of the user.

The novelty of the present invention condom retaining apparatus is that it is specially designed for retaining a condom which is extremely thin and highly flexible. The retaining apparatus is able to keep the condom in its unrolled position and withstand the natural movement during its usage, yet without tearing up the condom. One unique feature of the present invention condom retaining apparatus is that its attaching members are designed to be tightly affixed to the user's body part at locations very close to the body end of the user's penis, without the flexibility which may allow the condom to easily become loose.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 4 is a perspective back view showing the present invention condom retaining apparatus in use.

FIG. 5 is an enlarged perspective view of the present invention condom retaining apparatus showing the attachment.

FIG. 6 is a cross-sectional view taken along line 6—6 of FIG. 5.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
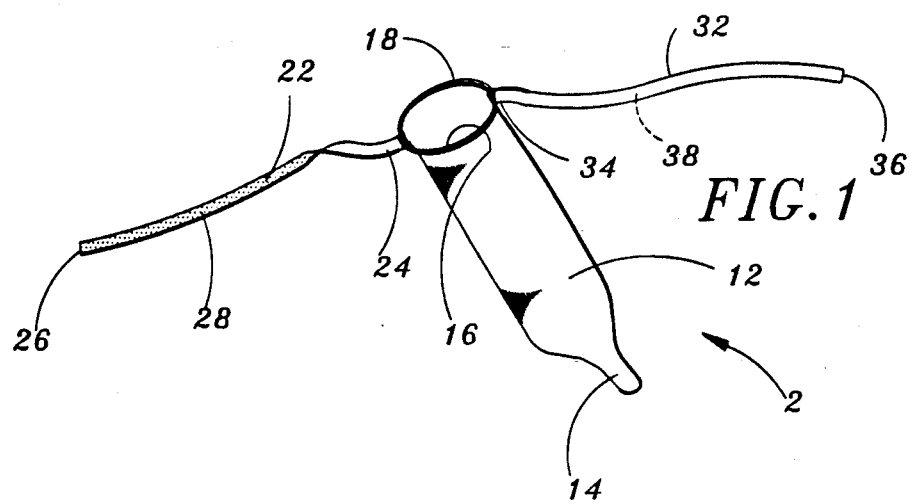
FIG. 1 is a perspective view of the present invention condom retaining apparatus.

Referring to FIG. 1, there is shown at 2 the present invention condom retaining apparatus. As shown in FIG. 1, a condom 12 has a closed end 14 and an open end 16. At the open end 16 of the condom 12, there is a condom ring 18 which is an integral part of the condom 12. There is provided a first elongated double-sided flexible thin band 22 which has a first end 24 and a second end 26, where the first end 24 is attached to the condom ring 18 at a first location, and the second end 26 is free. There is adhesive 28 provided on one side of the first elongated double-sided flexible thin band 22. Similarly, there is provided a second elongated double-sided flexible thin band 32 which also has a first end 34 and a second end 36, where the first end 34 is attached to the condom ring 18 at a second opposite location, and the second end 36 is free. There is also adhesive 38 provided on one side of the second elongated double-sided flexible thin band 32.

Figure 2:
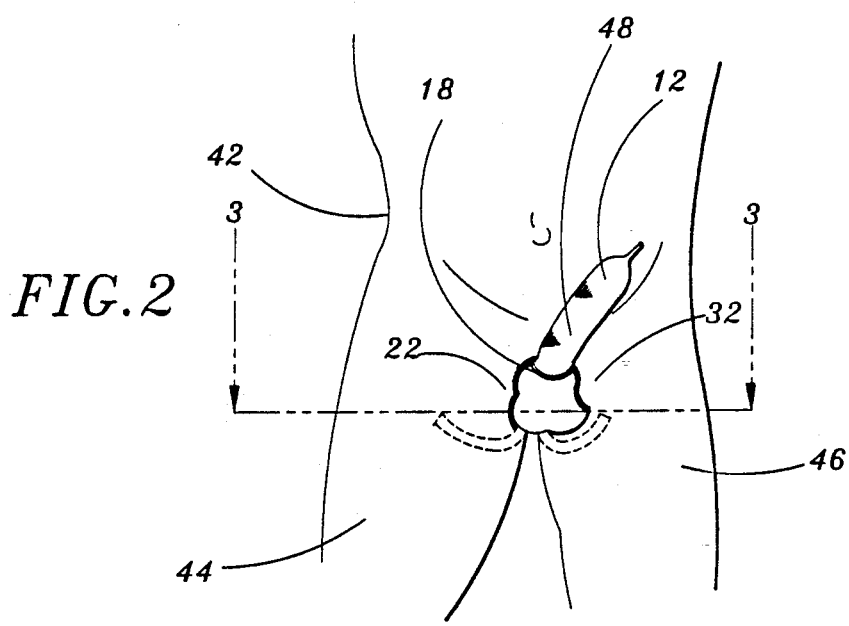
FIG. 2 is a perspective front view showing the present invention condom retaining apparatus in use.
Figure 3:
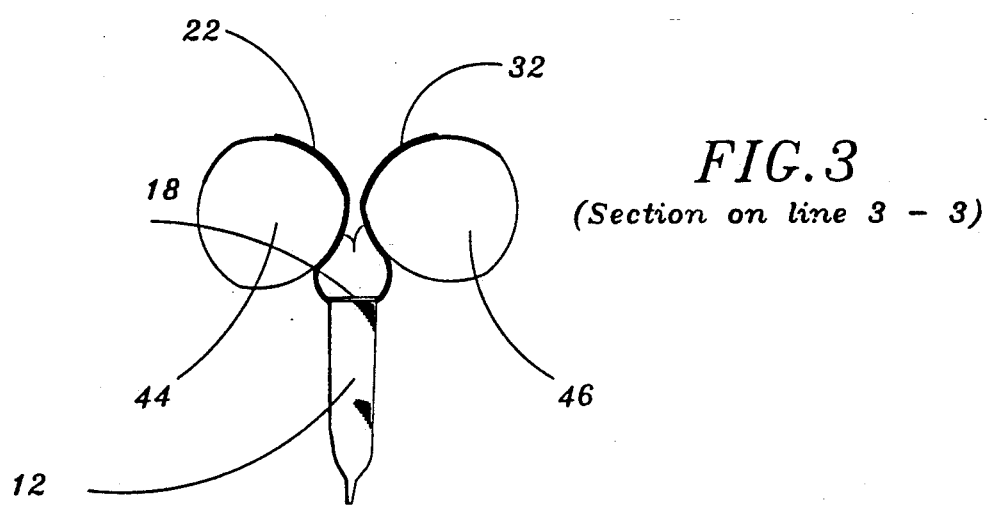
FIG. 3 is a cross-sectional view taken along line 3—3 in FIG. 2.

After a user 42 rolls the condom 12 on, he can apply the two elongated double-sided flexible thin bands 22 and 32 onto the skin of his two upper thighs 44 and 46 respectively. As shown in FIGS. 2, 3 and 4, the first elongated double-sided flexible thin band 22 can be affixed to the inner side of the user's first upper thigh 44 and adhered on the skin by the adhesive 28, and the second elongated double-sided flexible thin band 32 can be affixed to the inner side of the user's second upper thigh 46 and adhered on the skin by the adhesive 38. The first elongated double-sided flexible thin band 22 is wrapped around a portion of the user's first upper thigh 44 in the area immediately adjacent to the user's crotch area, and the second elongated double-sided flexible thin band 32 is wrapped around a portion of the user's second upper thigh 46 also in the area immediately adjacent to the user's crotch area. The respective second ends 26 and 36 of the first and second elongated double-sided flexible thin bands 22 and 32 extend backwardly and reach to the back of the user's upper thighs 44 and 46 respectively, immediately below the two buttocks of the user. It is important that the first and second elongated double-sided flexible thin bands 22 and 32 are affixed onto the inner side of the upper ends of the user's two legs. When the condom is placed onto the user's penis in its erect position, the first and second elongated double-sided flexible thin bands 22 and 32 are generally aligned in the direct opposite direction, which provides a maximum pull-back force onto the condom.

It is preferable to use such adhesive that will adhere not only to dry skin, but also to moist skin. By way of example, the first and second elongated double-sided flexible thin bands 22 and 32 are made of double-sided surgical tape, each having adhesive on one side. The adhesive is strong enough so that when the surgical tape is pressed against the user's skin, it will affix firmly on the user's skin; yet the adhesive is not too strong, so that after each usage the surgical tape can be easily peeled off the user's skin.

The adhesive 28 preferably covers the entire length of the first elongated double-sided flexible thin band 22. Similarly, the adhesive 38 preferably covers the entire length of the second elongated double-sided flexible thin band 32. The purpose of this arrangement is to have the entire first and second elongated double-sided flexible thin bands 22 and 32 affixed to the user's skin, including the first ends 24 and 34, so that the condom ring 18 of the condom 12 is restrained on the body end of the user's penis and has very little distance to travel. Alternatively, the adhesive 28 may cover the portion immediately adjacent to first end 24 of the first elongated double-sided flexible thin band 22, and the adhesive 38 may cover the portion immediately adjacent to first end 34 of the second elongated double-sided flexible thin band 32. This alternative arrangement will have the respective portions of the first and second elongated double-sided flexible thin bands 22 and 32, which portions are immediately adjacent to their respective first ends 24 and 34, affixed to the user's skin, so that the condom ring 18 of the condom 12 is restrained on the body end of the user's penis and has very little distance to travel. However, if the first and second elongated double-sided flexible thin bands 22 and 32 are disposed exactly in the fashion shown in FIGS. 2, 3, and 4, the adhesive 28 may be provide on the entire length of the first elongated double-sided flexible thin band 22 except the portion immediately adjacent to the first end 24, and the adhesive 38 may be provide on the entire length of the first elongated double-sided flexible thin band 32 except the portion immediately adjacent to the first end 34.

The key reason for the above arrangements being successful is that the two elongated double-sided flexible thin bands 22 and 32 are directly attached to the condom ring 18 of the condom 12, without any additional intermediate connecting straps or strings, whose flexibility may permit the condom to travel relative to the penis and thus become loose or come off the user's penis. In one embodiment of the present invention, the two first ends 24 and 34 of the two elongated double-sided flexible thin bands 22 and 32 are attached to the condom ring 18 of the condom 12 by a number of clipping members, as shown in FIGS. 5 and 6. The first end 24 of the first elongated double-sided flexible thin band 22 is folded around the condom ring 18 of the condom 12 at a first location, and clipped thereon by a first pair of small U-shaped clipping members 52 and 54. The first end 34 of the second elongated double-sided flexible thin band 32 is folded around the condom ring 18 of the condom 12 at a second location, which is opposite to the first location, and clipped thereon by a second pair of small U-shaped clipping members 56 and 58. These small U-shaped clipping members are made of harmless and durable materials such as metal or plastic. They are also small in size and light in weight so the user will hardly notice their existence. This is advantageous because it will not render any discomfort to the user, nor to his partner.

Another advantage of this present invention attachment is that it attaches the two elongated double-sided flexible thin bands 22 and 32 to the condom ring 18 of the condom 12, which is relatively strong, so that it will not tear up the condom 12 while it is in use.

The essential novel feature of the present invention condom retaining apparatus is that the condom is retained in optimum position by double-functioning bands. This means that each fastening band of the present invention condom retaining apparatus performs two functions simultaneously. The first function is attaching the apparatus to the user's body. The second function is attaching the condom. In prior art patents these two functions are performed by separate belts and straps. Most prior art patents utilize waist belts to perform the first function of attaching the apparatus to the user's body, then utilize additional intermediate connecting straps to perform the second function of attaching the urinary containers, where one end of such an additional intermediate connecting strap is attached to a urinary container and the other end is attached to the waist belt. As discussed before, this type of arrangement can be found in the Miller Patent, the Farrell Patent, the Gamard Patent, the Rasumny Patent and the Martin Patent. The disadvantage of this kind of arrangement is that although the waist belt is tightly fastened to a user's body, the additional intermediate connecting straps are not fastened to the user's body, but are dangling. Therefore their flexibility or elasticity will greatly increase the possibility of letting the condom become loose or fall off during sexual intercourse.

The present invention eliminates these additional intermediate connecting straps. The retaining bands of the present invention apparatus serve two functions: they are fastened to a user's body, as well as attached to the condom directly. While the bands of the present invention can still be flexible or elastic, they are fastened to the user's body without the freedom of dangling, and they are directly attached to the condom ring of the condom, so that the condom can be securely retained in its desired position. Based on this principle, there may be many alternative apparatus.

The present invention has many advantageous features, including (a) it is incorporated with the common structure of the condoms currently available on the market; (b) it is attached to the condom ring of the condom, which substantially reduces the chance of tearing up the condom; (c) it successfully retains the condom on its unrolled position while it is used, and therefore satisfies the various safety concerns; (d) it is easy to apply, and will not make a user uncomfortable; and (e) it is made of light weight harmless materials. In addition, it is inexpensive to produce, so that the final product will not cost substantially more than the current condom product.

Defined in detail, the present invention is a condom retaining apparatus, comprising: (a) a condom having an integral condom ring at its open end; (b) a pair of double-sided flexible thin bands each having a first end and a second end; (c) means for attaching said first ends of said pair of double-sided flexible thin bands to said integral condom ring of said condom at two opposite locations; and (d) means for attaching said pair of double-sided flexible thin bands to a portion of user's body; (e) whereby said condom retaining apparatus can keep said condom in its unrolled position while it is being used without tearing said condom and without being uncomfortable to the user.

In the preferred embodiments of the present invention defined in detail: (a) the means for attaching the first ends of the pair of double-sided flexible thin bands to the integral condom ring of the condom comprises small U-shaped clips; (b) the small U-shaped clips are made of thin metal wires or plastic material; (c) the means for attaching the pair of double-sided flexible thin bands to a portion of a user's body comprises adhesive members provided on at least one side of each of the pair of double-sided flexible thin bands for affixing the pair of double-sided flexible thin bands to the user's skin at the two inner upper thigh areas respectively; (d) the adhesive members are provided along the entire length of each of the pair of double-sided flexible thin bands, or along at least a substantial portion of each of the pair of double-sided flexible thin bands which are adjacent the condom; and (e) the pair of double-sided flexible thin bands are made of adhesive surgical tape.

Defined broadly, the present invention is a condom retaining apparatus, comprising: (a) a condom having an integral condom ring at its open end; (b) at least one flexible band having a first end and a second end; (c) means for attaching said first end of said at least one flexible band to said integral condom ring of said condom; and (d) means for attaching said at least one flexible band to at least a portion of a user's body; (e) whereby said condom retaining apparatus can keep said condom in its unrolled position while it is being used without tearing said condom and without being uncomfortable to the user.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A condom retaining apparatus, comprising:
   a. a condom having an open end, a closed end, a generally tubular shaped flexible thin sidewall, and an integral condom ring at the open end;
   b. a pair of double-sided flexible thin bands each having a first end and a second end, and a length between the first and second ends;
   c. means for attaching said first ends of said pair of double-sided flexible thin bands directly onto said integral condom ring of said condom at two opposite locations to avoid tearing apart said flexible thin sidewall of said condom and to spread and balance evenly a combination of forces exerted on said condom ring when said condom is being used;
   d. means for attaching said pair of double-sided flexible thin bands to a user's skin at an upper and inward area of one thigh of the user and an upper and inward area of a second thigh of the user respectively, the attaching means comprising adhesive members provided on at least one side of each of said pair of double-sided flexible thin bands; and
   e. wherein said means for attaching said first ends of said pair of double sided flexible thin bands to said integral condom ring of said condom comprises small U-shaped clips;
   f. whereby said condom retaining apparatus can keep said condom in an unrolled position while said condom is being used without tearing said condom and without rendering uncomfortableness to the user.

2. The invention as defined in claim 1 wherein said small U-shaped clips are made of thin metal wires.

3. The invention as defined in claim 1 wherein said small U-shaped clips are made of plastic material.

4. The invention as defined in claim 1 wherein said adhesive members are provided entirely along said at least one side of each of said pair of double-sided flexible thin bands.

5. The invention as defined in claim 1 wherein said adhesive members cover at least a substantial portion of said at least one side of each of said pair of double-sided flexible thin bands.

6. The invention as defined in claim 1 wherein said pair of double-sided flexible thin bands are made of adhesive surgical tape.

* * * * *